United States Patent [19]

Dedolph

[11] Patent Number: 5,455,220

[45] Date of Patent: Oct. 3, 1995

[54] CONCENTRATED PLANT GROWTH PROMOTER COMPOSITION COMPRISING N-6-BENZYLADENINE, AN ALCOHOL, AND A METAL HYDROXIDE

[75] Inventor: Richard B. Dedolph, Louisville, Ky.

[73] Assignee: Caudill Seed Company, Inc., Louisville, Ky.

[21] Appl. No.: 160,736

[22] Filed: Dec. 3, 1993

[51] Int. Cl.$^6$ .......................... A01N 25/02; A01N 25/22; A01N 43/90
[52] U.S. Cl. .......................... 504/241; 71/DIG. 1
[58] Field of Search ...................... 504/116, 241

[56] References Cited

U.S. PATENT DOCUMENTS

| | | | |
|---|---|---|---|
| 3,893,855 | 7/1975 | Charkoudian | 96/3 |
| 4,264,704 | 4/1981 | Borror et al. | 430/224 |
| 4,326,877 | 4/1982 | Kazutoyo | 504/241 |
| 4,387,155 | 6/1983 | Hill et al. | 430/217 |
| 4,489,152 | 12/1984 | Oberhauser et al. | 430/229 |
| 4,581,056 | 4/1986 | Noodén et al. | 504/241 |
| 4,902,332 | 2/1990 | Elliott et al. | 71/76 |

OTHER PUBLICATIONS

*The Farm Chemicals Handbook* "Potassium Hydroxide" p. B56 1987.

*Primary Examiner*—S. Mark Clardy

[57] ABSTRACT

Compositions for the regulation and promotion of the growth rate and characteristics of a variety of plants including N-6-Benzyladenine in a solubilizing agent which includes alcohol or a hydroxy compound such as a glycol and a selected hydroxide.

9 Claims, No Drawings

CONCENTRATED PLANT GROWTH PROMOTER COMPOSITION COMPRISING N-6-BENZYLADENINE, AN ALCOHOL, AND A METAL HYDROXIDE

BACKGROUND OF THE INVENTION

The present invention relates to liquid compositions including N-6-Benzyladenine (N6BA) for the purpose of promoting the growth and development of a wide variety of plant life.

N6BA has been recognized as an agent for promoting the growth and development of various types of plant life and is also used in some discrete, nonliving, chemical processes.

N6BA has also generally been demonstrated as physiologically effective in modifying plant growth and development of a myriad of plant species in many different ways. Responses elicited include promotion of cell division, inhibition of respiration, increasing retention of water and drought resistance, enhancing root and top growth with change in root/top ratios as well as shortening plant internodes which produces shorter bushier plants. The material has also been found to increase plant sugar content and enhancing color development and intensity in fruits and flowers while increasing the numbers of flowers.

Additionally, application of the material can increase chlorophyll retention in both pre and post harvest commodities and extends useable storage life of many fresh commodities while imparting a greater resistance to environmental stress.

The above noted advantageous effects are usually achieved by aqueous spray application of N6BA at low concentrations to field or greenhouse grown plants or as an aqueous dip applied to harvested commodities.

Some instances of application to preplanting seed treatment has been noted.

Working concentrations can be attained for spray application but considerable difficulty is experienced in attaining such field useable concentrations because of the low solubility of N6BA in known acceptable solvents. The low solubility ratios of N6BA has severely restrained its widespread use. In fact, the difficulty in compounding concentrates from which dilute spray solutions can be made along with the virtual impossibility of compounding super concentrates required for widespread field use with known techniques has generally relegated the use of the material to scientific investigation.

In order to be effective, N6BA must be applied as a dilute solution. However general use of N6BA has been hampered and virtually precluded in any application by the very low characteristic solubility of the material in water or other carriers. For example, at about 15 degrees C. the solubility of N6BA in water is limited to about 0.00044 grams per 100 milliliters which is far below a realistically useful level for commercial use.

It is known that the solubility of N6BA can be increased by the use of hydroxide in the water but even in such compositions the solubility is not increased to concentration levels practical for field concentrates and is not useful at all for super concentrates required for effective commercial use.

Ideally in order for a practical solution to be developed it is necessary to be able to produce a super concentrate. This reduces packaging and shipping cost since such a super concentrate can then be diluted to field concentrate levels with further dilution before application.

N6BA may be dissolved to approximately 5% concentration in mineral acids which are difficult to handle and many of which are inappropriate solvents for agricultural use. The N6BA can also be dissolved in alcohol-mineral acid solvent systems but still the solubility cannot be increased beyond the solubility in undiluted mineral acid.

Thus, no prior art composition has been developed to facilitate the manufacture of solutions of N6BA in commercially viable concentrations to allow shipment and subsequent dilution for use.

SUMMARY OF THE INVENTION

The present invention provides means for the formulation of concentrated compositions of N6BA which allow the material to be packaged and shipped in commercially practical quantities It has been unexpectedly found that the solubility of N6BA is dramatically increased in a solution of both alcohol or organic mono or poly hydroxy compounds such as a glycol or glycerine and a hydroxide. For example a solutions of up to approximately 50% N6BA can be formulated in an alcohol and a hydroxide soluble in the alcohol. Such a solution can provide commercially effective concentrations.

Thus, stock solutions containing N6BA can be produced and shipped for subsequent dilution and application Briefly the present invention provides compositions for the regulation and promotion of the growth rate and characteristics of a variety of plants including N-6-Benzyladenine in a solubilizing agent which includes alcohol or a hydroxy compound such as a glycol and a selected hydroxide.

Examples of solutions within the scope of the present invention are described hereinafter and graphically illustrated but it will be understood that the compositions discussed herein are not by way of limitation and that other compositions also within the scope of the present invention will occur to those skilled in the art upon reading the disclosure set forth hereinafter.

DETAILED DESCRIPTION OF EXAMPLES OF THE INVENTION

In one example in accordance with the present invention it was unexpectedly found that the solubility of N6BA in alcohol, in this case ethanol, was directly affected by the addition of quantities of a hydroxide soluble in the alcohol, in this case potassium hydroxide, as a co-solute, or by pre-dissolution in the alcohol solvent.

Further, it was found that the solubility of the N6BA in the alcohol/hydroxide solution was directly proportional to the Normality of the solution. In fact and approximate empirical relationship was developed which predicts that;

$\%S = .7N$ where % S is the per unit volume of N6BA expressed as a percentage and N is the Normality of the solution after dissolution of N6BA in the solution.

It will be recognized that the concentrations of N6BA available from the foregoing are dramatically and unexpectedly greater than with any previously available system.

The above equation indicates a direct concentration relationship between the Normality of the alcohol/hydroxide solution and concentration of N6BA. In the potassium hydroxide/ethanol system illustrated N6BA in excess of 60% have been achieved.

It is also recognized that for some purposes, such as bulk shipments, solutions with very high N6BA concentrations may be desirable.

However, for applications solutions having a concentration of 50% are more than adequate for direct dilution by users because with normal dilution ranges of the above concentration 1 liter of a 50% solution is sufficient to treat approximately 80 acres of turf or to formulate 83 cubic meters of growth regulator solution.

In one example in accordance with the present invention a highly useful 25% solution of N6BA can be produced by mixing 250 grams of N6BA with 84 grams of potassium hydroxide and diluting to 1 liter with ethanol.

While examples in accordance with the present invention have been described with reference to ethanol/potassium hydroxide solutions it has been found that other systems using alcohol with a hydroxide soluble in the alcohol are also effective to provide useful concentrations of N6BA.

It has also been recognized that monovalent hydroxides such as potassium hydroxide and sodium hydroxide have greater solubility in alcohol than di- or tri-, or higher valent hydroxides so are preferable to the higher valent hydroxides. For example, Potassium hydroxide is soluble on a weight basis of 33 parts to 100 parts of ethanol. Sodium hydroxide is soluble at a 14:100 ratio in ethanol and 24:100 ratio in absolute ethanol. Thus while data in the present application relates to ethanol/potassium hydroxide systems clearly other systems will also work.

Additionally, it has been found that in addition to alcohols a wide variety of water soluble polyhydroxy organic materials in which the hydroxide is soluble can also be used.

For example satisfactory concentrations of N6BA have been achieved using glycols such as glycerine, and propylene glycol as well as glycol ethers such as polyethylene glycol so long as the glycol is soluble in water and the hydroxide is also soluble in an aqueous solution of the hydroxy compound.

It will be understood that the foregoing is but one example of an arrangement within the scope of the present invention and that other arrangements also within the scope of the present invention will occur to those skilled in the art upon reading the disclosure set forth hereinbefore.

The invention claimed is:

1. Concentrated compositions for regulation and promotion of the growth rate and characteristics of plants comprising at least 2% N-6-Benzyladenine by weight in a soublizing agent comprised of at least 2% by weight of a water soluble organic hydroxy compound selected from the group consisting of ethanol, methanol, ethylene glycol, and polyethylene glycol, and at least 2% of a metal hydroxide soluble in a water solution.

2. The invention of claim 1 wherein said organic hydroxy compound is ethanol or methanol.

3. The invention of claim 1 wherein said metal hydroxide comprises a monovalent cation.

4. The invention of claim 2 wherein said organic hydroxy compound is ethanol.

5. The invention of claim 2 wherein said organic hydroxy compound is methanol.

6. The invention of claim 1 wherein said metal hydroxide is potassium hydroxide.

7. The invention of claim 1 wherein said metal hydroxide is sodium hydroxide.

8. The invention of claim 1 wherein said organic hydroxy compound is ethylene glycol.

9. The invention of claim 1 wherein said organic hydroxy compound is polyethylene glycol.

* * * * *